US009968312B2

(12) United States Patent
Cadwalader et al.

(10) Patent No.: US 9,968,312 B2
(45) Date of Patent: *May 15, 2018

(54) FLOOR MAT RADIATION ATTENUATION SHIELD

(71) Applicant: Worldwide Innovations & Technologies, Inc., Kansas City, KS (US)

(72) Inventors: John A. Cadwalader, Overland Park, KS (US); William Paul Radtke, Overland Park, KS (US)

(73) Assignee: Worldwide Innovations and Technologies, Inc., Kansas City, KS (US)

( * ) Notice: Subject to any disclaimer, the term of this patent is extended or adjusted under 35 U.S.C. 154(b) by 114 days.

This patent is subject to a terminal disclaimer.

(21) Appl. No.: 14/946,618

(22) Filed: Nov. 19, 2015

(65) Prior Publication Data

US 2016/0073981 A1    Mar. 17, 2016

Related U.S. Application Data

(63) Continuation of application No. 14/027,065, filed on Sep. 13, 2013, now Pat. No. 9,192,344.

(51) Int. Cl.
*H01J 35/16* (2006.01)
*A61B 6/10* (2006.01)
(Continued)

(52) U.S. Cl.
CPC ............... *A61B 6/107* (2013.01); *A61B 6/022* (2013.01); *A61B 6/4441* (2013.01); *A61B 6/485* (2013.01); *G21F 3/00* (2013.01)

(58) Field of Classification Search
CPC .... A61B 6/00; A61B 6/02; A61B 6/10; A61B 6/022; A61B 6/107; A61B 6/4441; H01J 35/16; G21F 3/00; G21F 1/00
(Continued)

(56) References Cited

U.S. PATENT DOCUMENTS 2,794,128 A    5/1957  Shasky
3,419,006 A   12/1968  King
(Continued)

FOREIGN PATENT DOCUMENTS

DE    30 17 640 A1   11/1981
DE    91 03 451 U1    9/1991
FR    2439460 A1     10/1978

OTHER PUBLICATIONS

International Search Report (Form PCT/ISA/210) for PCT/US02/05000 for Worldwide Innovations & Technologies, Inc., dated Jul. 11, 2002 (mailed Jul. 24, 2002), Authorized Officer: F. Jandl, 4 pages.

(Continued)

*Primary Examiner* — Jurie Yun
(74) *Attorney, Agent, or Firm* — Foley & Lardner LLP

(57) ABSTRACT

A system attenuates scatter radiation during a radiological procedure. The radiological procedure using a radiation machine including an emitter, a receiver, a base, and a table for a patient. The base is supported by a floor. The system includes a barrier formed of a radiation attenuation material and positioned over an area on the floor. The barrier is comprised of an elastomeric material and disposed beneath the table. The barrier on the floor can reduce substantial amounts of scatter radiation.

20 Claims, 3 Drawing Sheets

(51) Int. Cl.
*A61B 6/02* (2006.01)
*A61B 6/00* (2006.01)
*G21F 3/00* (2006.01)

(58) Field of Classification Search
USPC .............................. 378/42, 203; 250/515.1
See application file for complete search history.

(56) References Cited

U.S. PATENT DOCUMENTS

| | | | |
|---|---|---|---|
| 3,514,607 A | 5/1970 | Webster | |
| 3,935,099 A | 1/1976 | Weaver et al. | |
| 4,196,355 A | 4/1980 | Maine | |
| 4,286,170 A | 8/1981 | Moti | |
| 4,558,093 A | 12/1985 | Hatzenbuhler et al. | |
| 4,581,538 A | 4/1986 | Lenhart | |
| 4,621,808 A | 11/1986 | Orchard et al. | |
| 4,670,658 A | 6/1987 | Meyers | |
| 4,801,807 A * | 1/1989 | Jacobs .................... | A61N 1/16 250/515.1 |
| 4,938,233 A | 7/1990 | Orrison, Jr. | |
| 4,977,585 A | 12/1990 | Boyd | |
| 5,006,718 A | 4/1991 | Lenhart | |
| 5,038,047 A | 8/1991 | Still | |
| 5,097,497 A | 3/1992 | Deucher et al. | |
| 5,153,378 A * | 10/1992 | Garvy, Jr. ............... | A61N 1/16 174/384 |
| 5,247,182 A | 9/1993 | Servant et al. | |
| 5,278,219 A | 1/1994 | Lilley et al. | |
| 5,417,225 A | 5/1995 | Rubenstein et al. | |
| 5,523,581 A | 6/1996 | Cadwalader | |
| 5,525,408 A | 6/1996 | Weir et al. | |
| 5,548,125 A | 8/1996 | Sandbank | |
| 5,900,638 A | 5/1999 | Jaeger et al. | |
| 6,048,379 A | 4/2000 | Bray et al. | |
| 6,153,666 A | 11/2000 | Lagace | |
| 6,320,938 B1 | 11/2001 | Hopper | |
| 6,429,432 B1 | 8/2002 | McNaught et al. | |
| 6,456,684 B1 | 9/2002 | Mun et al. | |
| 6,481,888 B1 | 11/2002 | Morgan | |
| 6,674,087 B2 | 1/2004 | Cadwalader et al. | |
| 6,740,260 B2 | 5/2004 | McCurd | |
| 6,808,308 B2 | 10/2004 | Thompson | |
| 6,945,694 B2 | 9/2005 | Kantor et al. | |
| 6,967,343 B2 | 11/2005 | Batten et al. | |
| 7,099,427 B2 | 8/2006 | Cadwalader et al. | |
| 7,211,814 B2 | 5/2007 | Cadwalader et al. | |
| 7,473,919 B2 | 1/2009 | Cadwalader et al. | |
| 7,767,990 B2 | 8/2010 | Cadwalader et al. | |
| 8,022,378 B2 | 9/2011 | Cadwalader et al. | |
| 8,487,287 B2 | 7/2013 | Cadwalader et al. | |
| 9,192,344 B2 * | 11/2015 | Cadwalader ........... | A61B 6/022 |
| 2002/0109107 A1 | 8/2002 | Goldstein | |
| 2002/0148980 A1 | 10/2002 | Cadwalader et al. | |
| 2003/0209672 A1 | 11/2003 | Nelson et al. | |
| 2004/0041107 A1 | 3/2004 | Cadwalader et al. | |
| 2004/0105525 A1 | 6/2004 | Short et al. | |
| 2005/0258404 A1 | 11/2005 | McCord | |
| 2008/0119722 A1 | 5/2008 | Swaney | |
| 2008/0149864 A1 | 6/2008 | Hargrove | |
| 2009/0232282 A1 | 9/2009 | Belson et al. | |
| 2011/0095209 A1 | 4/2011 | Cadwalader et al. | |
| 2014/0151584 A1 | 6/2014 | Khandkar et al. | |

OTHER PUBLICATIONS

Advisory Action dated Jun. 24, 2010 for U.S. Appl. No. 10/978,680 (3 pages).
Final Office Action on U.S. Appl. No. 14/027,065, dated Apr. 1, 2015, 13 pages.
Fricke et al., "In-Plane Bismuth Breast Shields for Pediatric CT: Effects on Radiation Dose and Image Quality Using Experimental and Clinical Data", American Journal of Roentgenology, vol. 180, Feb. 2003, pp. 407-411 (5 pages).
International Search Report and Written Opinion for Application No. PCT/US2005/042685, dated Apr. 10, 2006, date received Apr. 13, 2006. 14 pages.
International Search Report and Written Opinion regarding International Appl. No. PCT/US2014/055196, dated Dec. 22, 2014, 12 pages.
Non-Final Office Action on U.S. Appl. No. 14/027,065, dated Oct. 27, 2014.
Notice of Allowance for U.S. Appl. No. 10/997,777, dated Jan. 10, 2007, 4 pages.
Notice of Allowance for U.S. Appl. No. 11/796,764, dated Sep. 8, 2008, 4 pages.
Notice of Allowance for U.S. Appl. No. 12/348,785, dated May 13, 2011, 8 pages.
Notice of Allowance for U.S. Appl. No. 12/852,287, dated Feb. 15, 2013, 10 pages.
Office Action for U.S. Appl. No. 10/997,777, dated Sep. 22, 2006, 6 pages.
Office Action for U.S. Appl. No. 11/796,764, dated Mar. 27, 2008, 7 pages.
Office Action for U.S. Appl. No. 12/348,785, dated Nov. 22, 2010, 6 pages.
Office Action for U.S. Appl. No. 12/852,287, dated Jul. 11, 2012, 13 pages.
Office Action for U.S. Appl. No. 12/852,287, dated Mar. 2, 2012, 12 pages.
Office Action for U.S. Appl. No. 90/010,808, dated Jul. 7, 2010, 8 pages.
Office Action for U.S. Appl. No. 90/010,808, dated Oct. 27, 2010, 6 pages.
Office Action for U.S. Appl. No. 90/010,809, dated Jul. 7, 2010, 7 pages.
Printout of copyright registration data for the Feb. 2003 issue of the American Journal Roentgenology obtained from the U.S. Copyright Office searchable copyright registrations indicating publication data of Jan. 22, 2003, 2 pages.
Request for Ex Parte Reexamination of U.S. Pat. No. 7,473,919 including exhibits, filed Jan. 5, 2010, 77 pages.
Request for Ex Parte Reexamination Of U.S. Pat. No. 7,211,814 including exhibits, filed Jan. 5, 2010, 123 pages.
U.S. Notice of Allowance on U.S. Appl. No. 14/027,065, dated Jul. 17, 2015, 9 pages.

* cited by examiner

FLOOR MAT RADIATION ATTENUATION SHIELD

CROSS REFERENCE TO RELATED PATENT APPLICATIONS

The present application is a continuation of U.S. application Ser. No. 14/027,065, filed Sep. 13, 2013, U.S. Pat. No. 9,192,344, which is related to U.S. Pat. No. 6,674,087, U.S. Pat. No. 7,099,427 and U.S. Pat. No. 8,487,287, which is a continuation-in-part of U.S. application Ser. No. 12/348,785, filed Jan. 5, 2009, which is a continuation application of U.S. application Ser. No. 11/796,764, filed Apr. 30, 2007, now U.S. Pat. No. 7,473,919, which is a divisional application of U.S. application Ser. No. 10/997,777, filed Nov. 24, 2004, now U.S. Pat. No. 7,211,814, the entire disclosures of which are hereby incorporated by reference in their entireties and assigned to the assignee of the present application.

BACKGROUND

The present disclosure relates generally to systems for and methods of attenuating radiation. More particularly, the present disclosure relates to systems for and methods of attenuating scatter radiation during a radiological examination of a patient.

Radiation barriers or shields are used to attenuate (e.g., deflect, absorb, etc.) the flux of electromagnetic radiation originating from a radiation source and directed towards a patient or medical personnel. Radiation can have beneficial and/or negative effects. One beneficial effect of radiation relates to radiological procedures (e.g., radiological examinations and treatments). For purposes of this disclosure, the phrase radiological examination refers generally to any procedure wherein radiation is applied to a patient for the purpose of producing an image or representation of the article (e.g., body part). Radiological examinations may provide a non-invasive means capable of obtaining an image of the internal composition of the patient. Radiological examinations may be employed in a variety of applications including, but not limited to, medical invasive and non-invasive procedures.

A wide array of medical procedures exist where radiological examinations are employed to obtain an image of the anatomy of a patient or portions thereof. For example, portions of a patient's anatomy may be irradiated during: (i) diagnostic procedures (e.g., Computed Tomography (CT) scanning, x-ray photography, or any other imaging procedure) allowing non-invasive investigation of anatomical regions of a patient (e.g., internal tissue, organs, etc.); or (ii) various invasive procedures, such as the fluoroscopic guidance and/or manipulation of instruments during surgical procedures (e.g., heart catheterization, etc.).

To obtain an image through a radiological examination, a primary radiation beam (i.e., entrance radiation) is applied to the patient. Preferably, radiation is selectively focused on to those areas to be examined (i.e., target areas) to minimize the patient's overall radiation exposure. Typically, the target areas are irradiated directly without any obstruction or impairment provided between the primary radiation beam and the patient. It is generally known to cover those areas distal, proximal, above and/or below the target area that are not being examined (i.e., secondary areas) with a radiation barrier or shield to prevent and/or reduce radiation exposure for those areas. Such shields are formed of a radiation attenuating material and are often placed directly upon the patient.

Scattered radiation or back scatter radiation occurs during radiological examinations. The radiation scattering involves radiation associated with the primary radiation beam deviating from a straight trajectory. This deviation is caused by radiation bouncing off objects (e.g, floors, walls, equipment, etc.) and people (e.g., patients and operators) within the examination room. The scattered radiation can expose medical personnel and patients to additional radiation.

Thus, there is a need to reduce exposure due to scattered radiation during a radiological procedure. Further, there is a need for a system for and a method of reducing scattered radiation during a medical procedure. Further, there is a need for a low cost system for and a method of reducing radiation exposure to personnel and patients present during radiological procedures. Further, there is a need for a radiation attenuation system and method that reduces scattered radiation and may be used during a radiological procedure without interfering with the clarity and/or accuracy of the provision of radiation. Further still, there is a need for a low cost, easy to use radiation attenuation system that is relatively adaptable for use with a variety of radiological procedures. It would be desirable to provide for a radiation attenuation system capable of satisfying one or more of these or other needs.

SUMMARY

An exemplary embodiment relates to a radiation attenuation system. The radiation attenuation system attenuates scatter radiation during a radiological procedure. The radiological procedure uses a radiation machine including an emitter, a receiver, a base and a table for a patient. The base is supported by a floor. The system includes a barrier formed of a radiation material and positioned over an area on the floor. The barrier being comprised of an elastomeric material and disposed beneath the table.

Another exemplary embodiment relates to a system for performing a radiation procedure. The system includes a radiation machine comprising an emitter disposed beneath the table. The system also includes a floor mat disposed beneath the table. The floor mat is comprised of a radiation attenuation material. The floor mat is partially disposed between the floor and the emitter.

Another embodiment relates to a method of performing a radiological procedure on a patient. The method includes placing a radiation attenuation mat on a floor beneath a table. The patient is disposed on the table for the radiological procedure. The method also includes providing radiation for the radiological procedure.

BRIEF DESCRIPTION OF THE DRAWINGS

Exemplary embodiments will hereafter be described with reference to the accompanying drawings, wherein like numerals denote like elements, and.

DETAILED DESCRIPTION

Referring generally to the FIGURES, a radiation attenuation system for use during radiological procedures is disclosed according to an exemplary embodiment. The radiation attenuation system is configured to attenuate scattered radiation. The system includes a floor mat for attenuating radiation that would otherwise reflect from the floor according to one embodiment. According to one embodiment, at least a first portion of the floor mat is configured to extend laterally from the table to further attenuate radiation and provide a softer surface for standing. The configuration of the floor mat (e.g., the shape, the radiation attenuation effectiveness, the thickness, the continuity, etc.) can be configured for various types of equipment or radiation procedures according to various embodiments.

The radiation attenuation floor mat may be used with any radiological procedure (e.g., fluoroscopy procedures, Computed Tomography (CT) procedures (e.g., invasive (fluoroscopy) and/or noninvasive (scanning), x-ray photography procedures, and/or any other image producing medical procedure using radiation, etc.)) where reduction of scattered radiation is desired. The radiation attenuation floor mat can be placed under the table upon which the patient undergoes the radiological procedure. The radiation attenuation floor mat reduces the amount of scattered radiation from the floor realized by a patient and/or personnel (e.g., physicians, surgeons, technicians, etc.) present during the procedures.

Figure 1:
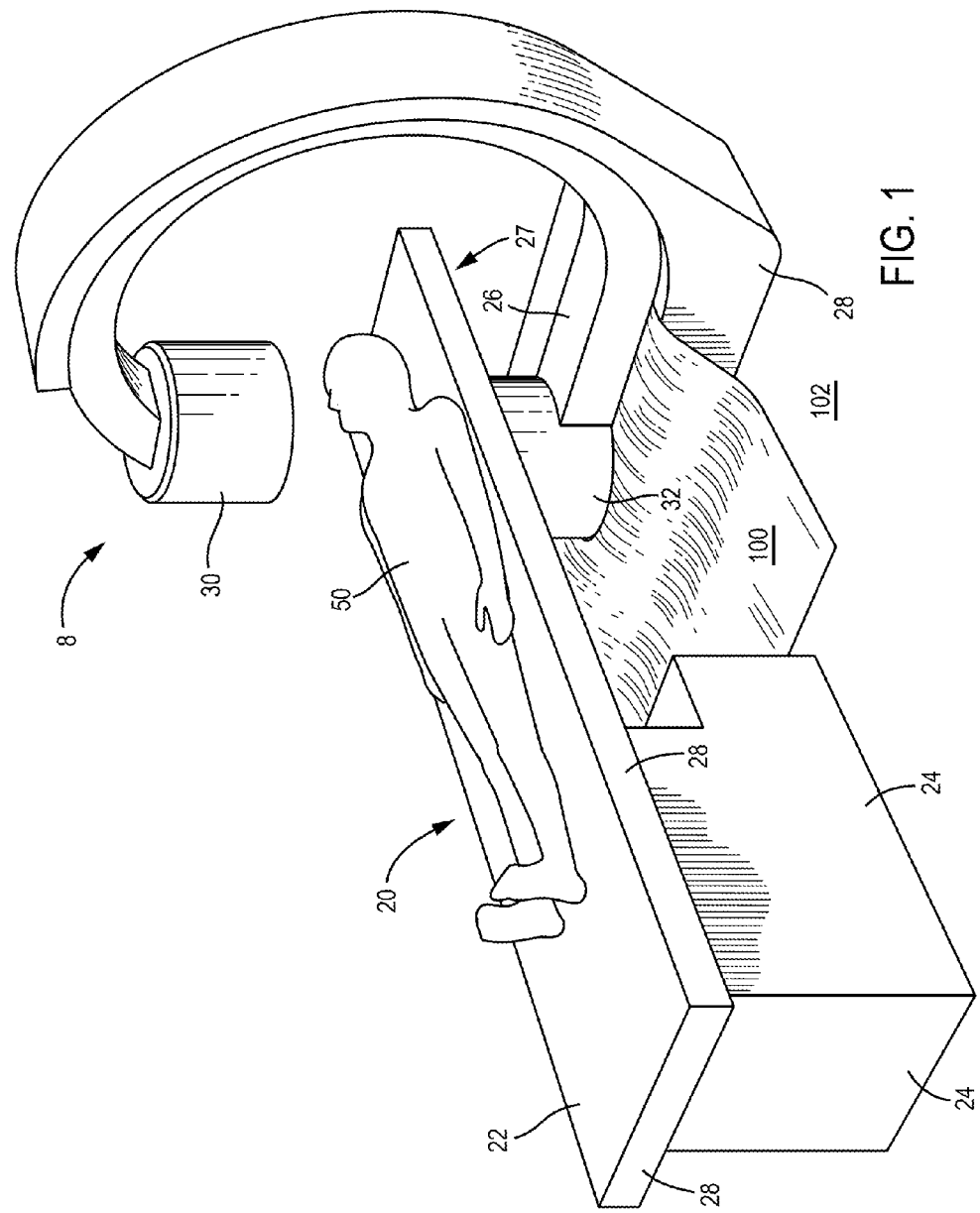
FIG. 1 is a perspective view schematic illustration of a radiation procedure system including a floor mat for reducing scattered radiation according to an exemplary embodiment.

Referring to FIG. 1, radiation system or machine 8 includes a table system 20 for a patient 50, a C-shaped support housing 28, and a C-shaped arm 26. C-shaped arm 26 is coupled to an emitter 32 and a receiver 30. C-shaped arm 26 can be moved within C-shape support housing 28 according to various positions for various radiation procedures.

Table system 20 includes a table 22 which is generally movable forward and backward through C-shaped arm 26 table 22 can also be tilt-able. Table system 20 also includes a table support 24. Table support 24 is generally substantial and can include drawers. Table system 20 can be configured in various fashions. Generally, table system 20 is shaped such that there is an exposed portion of floor 102 underneath table 22.

Figure 2:
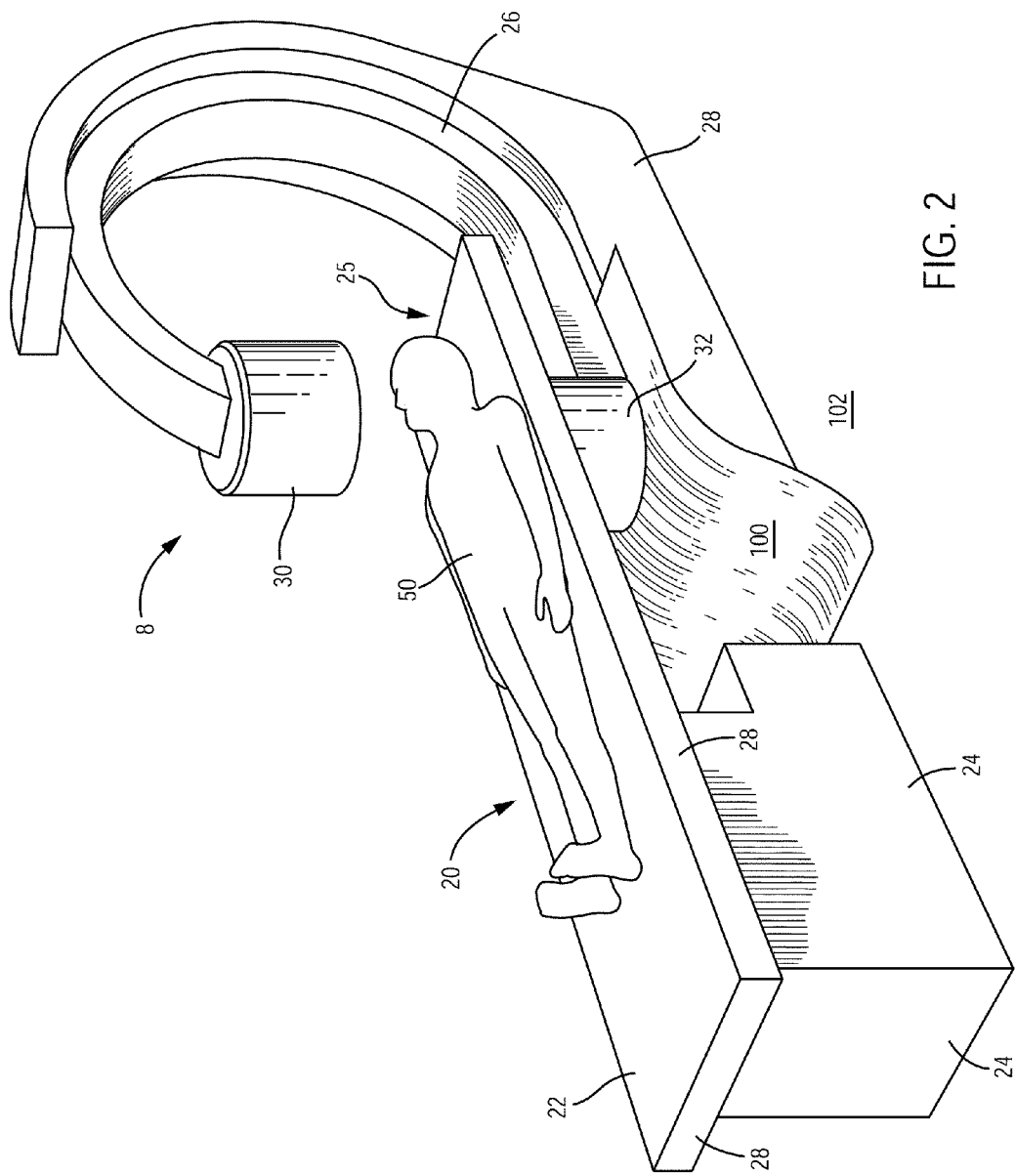
FIG. 2 is a perspective view schematic illustration of a radiation procedure system including a floor mat for reducing scattered radiation according to another exemplary embodiment.

With reference to FIG. 2, radiation machine 8 includes C-shaped support housing 28 and C-shaped arm 26 provided in a different orientation than shown in FIG. 1. In FIG. 2, C-shaped support housing 28 is provided about a head end 25 of table 22 while support housing 28 is provided about a lateral side 27 of table 22 in FIG. 1. The configurations of machine 8 or not shown in a limiting fashion, Machine 8 can be of various shapes, sizes, configurations, etc. and can be positioned at other locations around table 22 without departing from the scope of the invention.

A floor mat 100 is disposed on a floor 102 beneath radiation machine 8 in FIGS. 1 and 2. Floor mat 100 advantageously reduces back scatter radiation or scattered radiation according to one embodiment. Floor mat 100 can be provided between emitter 32 and support housing 28 and above floor 102 as shown in FIG. 1 according to one embodiment. With reference to FIG. 2, mat 100 can be provided underneath support housing 28 between floor 102 and support housing 28 in one embodiment. In one embodiment, floor mat 102 covers an area or portion of exposed floor under table 22 near where an operator stands.

In one embodiment, floor mat 100 is a three foot by five foot mat, four foot by six foot mat, or four foot by seven foot mat of radiation attenuating material. In one embodiment, mat 100 has an area between 4 square feet and 28 square feet or more. In one embodiment, mat 100 has an area of more than 8 square feet. Mat 100 can be rectangular, L-shaped, or have curved edges depending upon design criteria for machine 8 and the room for machine 8. The radiation attenuating material can be any of the materials disclosed in the patents incorporated by reference or materials such as materials for RADPAD® shields provided by Worldwide Innovations and Technologies, Inc.

Mat 100 is between 1/64 of an inch to 1 inch thick in one embodiment, although other thicknesses can be utilized. In one embodiment, mat 100 includes barrier material with a thickness between 1/16 to 1/8 of an inch. In one embodiment, mat 100 includes a covering and mat 100 including the covering has a thickness between 1/8 to 1/4 of an inch. In one embodiment, floor mat 100 is elastomeric, thereby providing a soft surface for standing. The durometer of floor mat 100 can be similar to the durometer used for radiation shields disclosed in U.S. Pat. No. 4,938,233, which is hereby incorporated by reference in its entirety. Floor mat 100 extends to the edge of table 22 and can extend a foot or more beyond the edge of table 22 on the lateral side of table 22 so that an operator can stand on the soft surface during the procedure and during procedure set-up and conclusion. In one embodiment, floor mat 100 extends at least 1 foot beyond both lateral sides of table 22.

Figure 3:
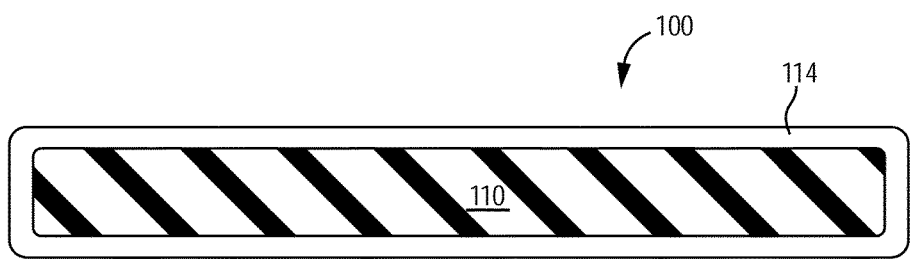
FIG. 3 is a cross-sectional view schematic illustration of a floor mat comprised of radiation attenuation material for reducing scattered radiation in the systems illustrated in FIGS. 1 and 2 according to another exemplary embodiment.

With reference to FIG. 3, a cross sectional view of floor mat 100 includes a layer 110 (e.g., platform, web, matrix, film, barrier or pad of radiation attenuating material). Layer 110 can be provided with a spacer, filler, lifter, relatively non-radiation attenuating material, etc. Floor mat 100 can also include layer 114 (e.g., housing, casing, coating, skin, outer material, membrane, etc.), shown as a cover. Layer 114 forms the exterior portion or surface (e.g., exposed surface, etc.) of mat 100 protecting layer 110 from contaminants (e.g., fluids, particles, etc.), providing enhanced comfort for the operator, and/or improving the overall durability of mat 100. Layer 110 can include air bubble or other voids to reduce weight and increase softness and pliability.

Radiation shields can also be provided about various components associated with machine 8. For example, barriers can be provided as drapes around outside edges 28 of table 22 to further reduce back scatter radiation. In addition, barriers can be hung around components such as emitter 32 and receiver 30 as well as other areas which may be sources of scatter radiation. In one embodiment, barrier drapes hang from a top surface of table 22 to floor 102. In another embodiment, barrier drapes hang a shorter distance from the top surface of table 22 or are attached to a bottom surface of table 22. The barriers can be hung using VELCRO® fasteners, tape, snaps, buckles, etc. The barriers can be comprised of any of the materials disclosed in the patents incorporated by reference or materials for RADPAD® shields provided by Worldwide Innovations and Technologies, Inc.

Floor mat 100 may be configured to attenuate the flux of electromagnetic radiation over a broad wavelength range depending on the intended application. For example, floor mat 100 may attenuate radiation from wavelengths of around $1.0 \times 10^{-15}$ meters (e.g., cosmic rays) to around $1.0 \times 10^6$ meters (e.g., radiation from AC power lines) including visible and invisible light, and may find incidental uses in relatively low or high frequency extremes (including gamma rays). The degree of radiation transmission attenuation factor by floor mat 100 will depend in part on the specific application to which mat 100 is utilized. According to an exemplary embodiment, layer 110 has a radiation attenuation factor that remains substantially constant throughout the entire layer.

According to one embodiment, mat 100 has a radiation attenuation factor of a percent (%) greater than about 10% of a primary 100 kVp x-ray beam. According to other suitable embodiments, mat 100 has a radiation attenuation factor of a percent of about 10-50%. According to further suitable embodiments, mat 100 has a radiation attenuation factor greater than about 50%, suitably greater than about 90%, suitably greater than about 95%, at least in the area configured to cover floor 102. According to a preferred embodiment, floor mat 100 has a radiation attenuation factor of around 20-60%. According to still further suitable embodiments, mat 100 may have radiation attenuation factors less than 10% or greater than 95% depending on the application. Floor mat 100 may also at least partially attenuate gamma rays, and may have a gamma ray attenuation fraction of at least about 10% of a 140 keV gamma radiation source.

Mat 100 and layer 110 may be fabricated from of any radiation attenuation material including, but not limited to, bismuth, barium, lead, tungsten, antimony, copper, tin, aluminum, iron, iodine, cadmium, mercury, silver, nickel, zinc, thallium, tantalum, tellurium, and/or uranium. Any one of the aforementioned attenuation materials alone or in a combination of two or more of the attenuation materials may provide the desired attenuation.

Layer 110 may have a composition that includes only a radiation attenuation material or combinations thereof, or alternatively, floor mat 100 may have a composition that includes a combination of a radiation attenuation material and a non-radiation attenuating material. For example, layer 110 may include one or more radiation attenuation materials compounded (e.g. mixed, blended, alloyed, dispersed, layered, etc.) with a relatively non-radiation attenuating carrier material. According to one embodiment, layer 110 has non-elastomeric composition similar to the radiation attenuation system disclosed in U.S. Pat. No. 4,938,233, which is hereby incorporated by reference in its entirety. According to another embodiment, layer 110 has a composition similar to the radiation attenuation system disclosed in U.S. Pat. No. 6,674,087, which is hereby incorporated by reference in its entirety. However, it should be noted that layer 110 is not limited to such embodiments. Layer 110 can be provided as a relatively single body, or alternatively may include a plurality of members (e.g., multiple layers of attenuating films or sheets stacked (e.g., overlapping) relative to each other).

According to one embodiment, layer 110 is a relatively light weight and flexible. Floor mat 100 as a flexible member allows provides for optimized workability for processing, bending, folding, rolling, shipping, etc. Mat 100 may be formable (e.g. deformable) or compliant, and relatively stretchable (e.g. elastic) according to one embodiment. In this manner, mat 100 can advantageously conform to the contours of support housing 28 according to one embodiment.

Figure 4:
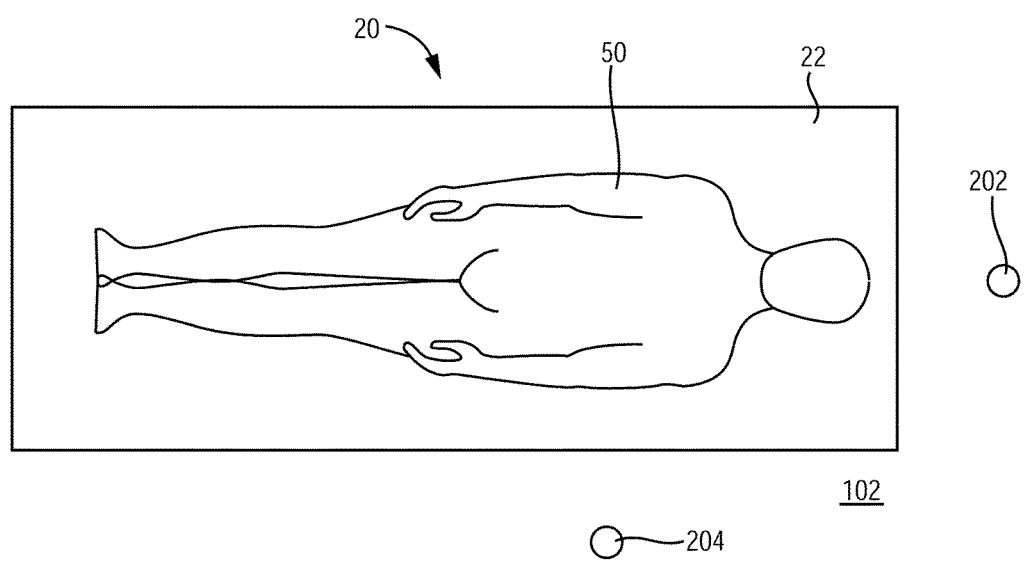
FIG. 4 is a top view schematic illustration of a table for the radiation procedure systems illustrated in FIGS. 1 and 2 showing sensor placement for radiation sensor readings with and without the floor mat illustrated in FIG. 3.

With reference to FIG. 4, table system 20 was used with radiation machine 8 to test attenuation by floor mat 100 according to an Example I of test data. In Example I, floor mat 100 included two layers of RADPAD material having a total thickness of approximately 1/16 of an inch, and was a 4'×6' rectangular mat. A sensor 202 and a sensor 204 were placed approximate radiation machine 8 in Example I. Radiation machine 8 was a GE 9800 C-Arm in Example I arranged with mat 100 as shown in FIG. 1.

According to Example I, sensor 202 was placed above a top of table 22 at heights of 12", 24" and 36" off floor 102, and sensor 204 was placed at heights of 36", 48" and 60" off of floor 102 at a side of table 22 associated with a left side (from the orientation of patient 50 lying on the patient's back). Sensors 202 and 204 are Unfors EDDS-30 dosimeters in Example 1. A patient was present on table 22 when readings were taken and a table skirt was not included in Example I.

With reference to Table I below, sensors 202 and 204 recorded radiation at the 36" level, the 48" level and the 60" level using mat 100 and not using mat 100 according to Example I. A skirt was not provided around table 22. As shown in Table I, radiation reductions of 53%-94% were achieved in three readings of sensor 204 at a sensor position of 60" off the floor, radiation reductions of 0%-80% were achieved in three readings of sensor 204 of sensor 204 at a position of 48" off the floor, and radiation reductions of 62%-98% were achieved in three readings of sensor 204 at a location of 36" off the floor. Radiation reductions of 60%-14% were achieved in three readings with sensor 202 12" off the floor, and radiation reductions of 87%-96% were achieved in three readings of sensor 202 at a sensor position of 24" off the floor, and radiation reductions of 52%-58% were achieved in two readings at sensor position 202 being 36" off the floor. A third reading for the 36" position off the floor was not recorded in Table I.

Table I shows significant reduction due to the use of the mat 100 according to Example 1.

TABLE I

| SENSOR 204 Sensor Position-Patient's Left Side | | | |
|---|---|---|---|
| Readings in μRads/minute | A | B | C |
| No Mat/No Skirt | | | |
| Left of Table 36" off the floor Mat/No Skirt | 1,920 | 1,776 | 5,460 |
| Left of Table 36" off the floor % Reduction | 734 62% | 298 84% | 115 98% |
| Readings in μRads/minute | A | B | C |
| No Mat/No Skirt | | | |
| Left of Table 48" off the floor Mat/No Skirt | 228 | 1,026 | 1,674 |
| Left of Table 48" off the floor % Reduction | 3,024 0% | 309 67% | 253 80% |
| Readings in μRads/minute | A | B | C |
| No Mat/No Skirt | | | |
| Left of Table 60" off the floor | 570 | 870 | 5,767 |

TABLE I-continued

Mat/No Skirt

| | | | |
|---|---|---|---|
| Left of Table 60" off the floor | 270 | 315 | 348 |
| % Reduction | 53% | 64% | 94% |

SENSOR 202
Sensor Position-Patient's Left Side

| | | | |
|---|---|---|---|
| Readings in μRads/minute | A | B | C |
| No Mat/No Skirt | | | |
| Head of Table 12" off the floor Mat/No Skirt | 2,860 | 1,512 | 924 |
| Head of Table 12" off the floor % Reduction | 1,143 60% | 634 58% | 793 14% |
| Readings in μRads/minute | A | B | C |
| No Mat/No Skirt | | | |
| Head of Table 24" off the floor Mat/No Skirt | 1,908 | 2,055 | 3,413 |
| Head of Table 24" off the floor % Reduction | 432 87% | 408 80% | 122 96% |
| Readings in μRads/minute | A | B | C |
| No Mat/No Skirt | | | |
| Head of Table 36" off the floor Mat/No Skirt | 765 | 513 | |
| Head of Table 36" off the floor % Reduction | 372 52% | 216 58% | 113 |

It is important to note that the construction and arrangement of the elements of the radiation attenuation system as shown in the illustrated embodiments is illustrative only. Although only a few embodiments of the present inventions have been described in detail in this disclosure, those skilled in the art who review this disclosure will readily appreciate that many modifications are possible (e.g., variations in sizes, dimensions, structures, shapes and proportions of the various elements, values of parameters, mounting arrangements, use of materials, colors, orientations, etc.) without materially departing from the novel teachings and advantages of the subject matter recited. For example, elements shown as integrally formed may be constructed of multiple parts or elements shown as multiple parts may be integrally formed, the operation of the interfaces may be reversed or otherwise varied, or the length or width of the structures and/or members or connectors or other elements of the system may be varied.

Also, for purposes of this disclosure, the term "coupled" means the joining or combining of two members (e.g., portions, layers, materials, etc.) directly or indirectly to one another. Such joining or combining may be stationary in nature or movable in nature. Such joining may be achieved with the two members or the two members and any additional intermediate members being integrally formed as a single unitary body with one another or with the two members or the two members and any additional intermediate member being attached to one another. Such joining or combining may be permanent in nature or alternatively may be removable or releasable in nature.

Components of mat 100 are preferably non-toxic, recyclable, and/or biodegradable. According to an alternative embodiment, the articles of radiation attenuation system may be reusable (e.g. for attenuation of radiation from atomic/nuclear disaster, clean up, rescue operations, etc.). According to a preferred embodiment, the articles of mat 100 (e.g., layers 110 and 114) may be sterilized between uses to minimize the likelihood of bacteriological or virus contamination. Sterilization may be performed in any convenient manner, including gas sterilization and irradiation sterilization.

It should further be noted that the elements and/or assemblies of the system may be constructed from any of a wide variety of materials that provide sufficient strength or durability, in any of a wide variety of colors, textures and combinations. Accordingly, all such modifications are intended to be included within the scope of the appended claims. Other substitutions, modifications, changes and omissions may be made in the design, operating conditions and arrangement of the preferred and other exemplary embodiments without departing from the spirit of the appended claims.

The order or sequence of any process or method steps may be varied or re-sequenced according to alternative embodiments. In the claims, any means-plus-function clause is intended to cover the structures described herein as performing the recited function and not only structural equivalents but also equivalent structures. Other substitutions, modifications, changes and omissions may be made in the design, operating configuration and arrangement of the preferred and other exemplary embodiments without departing from the spirit of the inventions as expressed in the appended claims.

What is claimed is:

1. A system for attenuating scatter radiation during a radiological procedure using a radiation machine including an emitter, a receiver, a base, and a table for a patient, the base being supported by a floor, the system comprising:
    a barrier formed of radiation attenuation material, the barrier having a durometer of less than 100 shore "00" and being configured to fit below the table, be disposed over an area on the floor, and extend from the table at an operator position.

2. The system of claim 1, wherein the barrier is provided between a support for the table and the base of the radiation machine.

3. The system of claim 2, wherein the barrier extends past a lateral side of the table.

4. The system of claim 3, wherein the barrier extends past the lateral side by a distance of at least one foot.

5. The system of claim 1, wherein the barrier is L-shaped.

6. The system of claim 5, wherein the barrier is comprised of an elastomeric matrix.

7. The system of claim 6, wherein an operator stands on at least a portion of the barrier during the procedure.

8. The system of claim 1, wherein the barrier is placed partially over the base of the radiation machine.

9. The system of claim 8, wherein the base of the radiation machine is C-shaped.

10. The system of claim 9, wherein the barrier is between 0.03 and 1.0 inches thick.

11. The system of claim 1, wherein the barrier has an area of at least 8 square feet.

12. The system of claim 1, wherein the table includes a radiation attenuation skirt.

13. The system of claim 1, wherein the barrier is provided under the emitter and above the base of the radiation machine at a location of the emitter.

14. A system for use with a radiation machine comprising an emitter disposed beneath a table for performing a radiation procedure, the system comprising:

a floor mat configured to be disposed beneath the table and over an area on a floor, the floor mat being comprised of radiation attenuation material, the floor mat being between ⅛ and ¼ of an inch thick.

15. The system of claim 14, wherein the radiation machine is a fluoroscope.

16. The system of claim 15, wherein the floor mat is configured to fit between the emitter and a bottom portion of a C-shaped support base of the radiation machine.

17. The system of claim 16, wherein the floor mat extends past a lateral side of the table by at least one foot.

18. A method of performing a radiological procedure on a patient, the method comprising:
    placing a radiation attenuation mat on a floor beneath a table, wherein the patient is disposed on the table for the radiological procedure; and
    providing radiation to the patient, wherein the radiation attenuation mat reduces 53% to 95% of radiation level tested at a position 60 inches from the floor.

19. The method of claim 18, wherein the radiation attenuation mat reduces scatter radiation at a location off a head of the patient by more than 25 percent.

20. The method of claim 18, wherein the radiation attenuation mat reduces scatter radiation at a location off the left side of the patient by more than 25 percent.

* * * * *